United States Patent [19]

Chern

[11] Patent Number: 4,755,753

[45] Date of Patent: Jul. 5, 1988

[54] EDDY CURRENT SURFACE MAPPING SYSTEM FOR FLAW DETECTION

[75] Inventor: Engmin J. Chern, West Chester, Ohio

[73] Assignee: General Electric Company, Cincinnati, Ohio

[21] Appl. No.: 887,303

[22] Filed: Jul. 23, 1986

[51] Int. Cl.⁴ .................... G01N 27/90; G01R 33/12
[52] U.S. Cl. .................................... 324/237; 324/240; 324/243
[58] Field of Search ............... 324/233, 236, 237–243, 324/226, 225, 260–262, 228, 263

[56] References Cited

U.S. PATENT DOCUMENTS

| | | | |
|---|---|---|---|
| 3,302,105 | 1/1967 | Libby et al. | 324/233 |
| 3,475,681 | 10/1969 | Nerwin, Jr. et al. | 324/226 |
| 3,737,764 | 6/1973 | Dufayet | 324/237 |
| 3,826,132 | 7/1974 | Fetner et al. | 73/143 |
| 4,126,491 | 11/1978 | Karlsson | 324/238 X |
| 4,194,149 | 3/1980 | Holt et al. | 324/220 |
| 4,247,818 | 1/1981 | Hiroshima et al. | 324/202 |
| 4,268,791 | 5/1981 | Rogel et al. | 324/238 |
| 4,322,683 | 3/1982 | Vieira et al. | 324/225 |
| 4,337,431 | 6/1982 | Hale | 324/238 X |
| 4,476,434 | 10/1984 | Collins et al. | 324/226 X |
| 4,481,471 | 11/1984 | Miller et al. | 324/240 |
| 4,495,587 | 1/1985 | Plante et al. | 324/226 X |
| 4,596,953 | 6/1986 | Nagasaka et al. | 324/242 |
| 4,641,092 | 2/1987 | Sakamoto et al. | 324/236 X |

Primary Examiner—Reinhard J. Eisenzopf
Assistant Examiner—Warren S. Edmonds
Attorney, Agent, or Firm—Nathan D. Herkamp; Derek P. Lawrence

[57] ABSTRACT

A system and method for nondestructive testing of a part using eddy current impedance measuring techniques. An eddy current probe is positioned above the surface of the part for measuring an induced eddy current signal and generating an electrical signal representative thereof. A first and second movement signal is generated representative of a first and second scan direction of the probe. Relative movement is effected between the probe and the part, whereby the probe scans the part for producing electrical signals varying as a function of eddy current signal. The electrical signals are converted to mutually perpendicular drive signals representative of the eddy current signature at a corresponding location of the part. The first and second movement signals are combined with the mutually perpendicular drive signals of and second composite signal which varies as a function of the movement of the probe and eddy current signal. The first and second composite signals are applied to a display means for generating a three-dimensional image representative of irregularities in the part.

17 Claims, 9 Drawing Sheets

OSCILLOSCOPE DISPLAY
PRIOR ART

EDDY CURRENT SURFACE MAPPING SYSTEM FOR FLAW DETECTION

FIELD OF THE INVENTION

This invention generally relates to a system and method for nondestructive testing of manufactured parts using eddy current impedance measuring techniques, and more particularly, to a system and method for determining irregularities in the part by generating a three-dimensional image using eddy current signals.

BACKGROUND DISCUSSION

One of the primary considerations in designing a structure is that the strength must be sufficiently greater than the stress to assure both safety and reliability. In manufactured parts, the capability of directly mapping out the critical areas where stresses, defects, flaws, cracks, or inclusions occur is extremely important for determining the structural integrity of the part.

Several methods of detecting irregularities in manufactured parts have been developed over the years using high powered optical techniques, ultrasonic surface wave measurement, stress fluorescent penetrant techniques and eddy current inspection analysis. This invention is primarily concerned with detection of irregularities in manufactured parts using eddy current inspection analysis.

A number of different methods and devices for eddy current detection of flaws in electrically conductive parts are already known and are described in particular in U.S. Pat. Nos. 3,737,764, 4,194,149, 3,826,132, 3,475,681 and 4,268,791.

Figure 1:
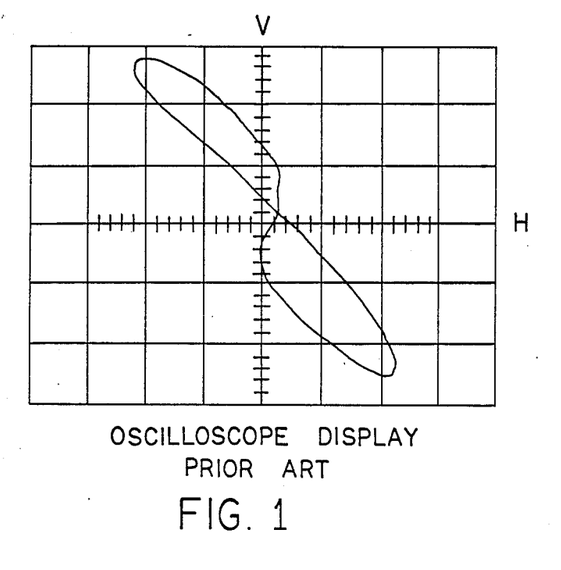
FIG. 1 illustrates the display of an eddy current signature for the prior art.

A problem in the prior art has been the display of the eddy current signals in a form which is easily understandable by technicians and users of eddy current inspection methods. The most common form of displaying eddy current results is to use an oscilloscope for displaying eddy current signatures as an eddy current probe traverses the surface of a part. The eddy current probe, upon traversing a flaw generates a signal displayed on the scope representative of some of the characteristics and the type of anomaly detected. A typical display pattern presented on the scope is the two-lobed signal generated by the sensor, as shown in FIG. 1. The display pattern changes with the defect detected in the metallic part. A great deal of previous experience and knowledge of the display pattern and the electrical properties of the material is required for determining the type of flaw represented by this type of display pattern. This invention overcomes previous problems by presenting a three-dimensional image of the surface of a part as an eddy current probe scans the part for identifying defects in the part.

SUMMARY OF THE INVENTION

Among the several objects of the present invention may be noted the provision of a system and method of displaying eddy current signatures on a display device, the provision of such system and method in which the material surface of the manufactured part is graphically mapped for displaying various defects of the manufactured part, and the provision of such system and method for exactly mapping the stress distributions and defect locations in a part.

It is another object of the present invention to enhance eddy current inspection capabilities by displaying a three-dimensional surface representation of irregularities in the manufactured part. These as well as other objects and advantageous features of the present invention will be in part apparent and in part pointed out hereinafter.

In general, a system and method is provided for nondestructive testing of a part using eddy current impedance measuring techniques for detecting induced changes of electrical conductivity and magnetic permeability due to residual stresses and defects in electrically conductive materials.

In the method, an electro-magnetic transducer, such as an eddy current probe, is positioned near the surface of the part for measuring an induced eddy current signal and generating an electrical signal representative thereof. A first and second movement signal is generated representative of a first and second scan direction of the probe. Relative movement is effected between the probe and the part, whereby the probe scans the part for producing electrical signals varying as a function of eddy current signal. The electrical signals are converted to mutually perpendicular drive signals representative of the eddy current signature at a corresponding location of the part. One of the first and second movement signals is combined with the mutually perpendicular drive signals of the eddy current signature for generating a composite signal which varies as a function of the movement of the probe and eddy current signature. The composite signal and the other of the first and second movement signals are applied to a display means for generating a three-dimensional image representative of irregularities in the part.

Also in general in one form of the invention, the invention makes use of the fact that irregularities are often known from previous experience to only occur in specific locations for a given part. A method is provided for testing of suspected irregularities in a part where irregularities are likely to occur. An eddy current probe is positioned for scanning an area previously identified from testing a plurality of manufactured parts as a likely area of irregularities. The part is positioned such that the identified area of the part is exposed to the eddy current probe. The location is scanned for generating a three-dimensional display of any irregularity in the manufactured part. The image is then analyzed for determining the type of irregularity.

In particular, the system includes an electromagnetic transducer, such as an eddy current probe, positioned for inducing an eddy current in the part and detecting an output signal representative of the induced eddy current impedance. The system uses a scanning apparatus for effecting relative movement between the transducer and the part. A processing apparatus such as an eddyscope, produces first and second drive signals in response to the output signal from the eddy current probe. The eddyscope, using eddy current impedance measuring techniques, detects the induced changes of the electrical conductivity and magnetic permeability due to residual stresses and defects in the electrically conductive material. A controller means such as a numerical controller, produces a first and a second movement signal for controlling incremental movements in mutually perpendicular directions for the scanning apparatus. The first and second drive signals and one of the first and second movement signals are summed for generating a composite signal. The composite signals is representative of the eddy current vector components and their location in the part. A an apparent display responsive to the composite signal generates a three-dimensional image of the surface from the composite signal for mapping out the stress distributions and defects of the part.

The exemplification set out herein illustrate the preferred embodiment of the invention in one form thereof, and such exemplifications are not to be construed as limiting either the scope of the invention in any manner.

DETAILED DESCRIPTION OF AN ILLUSTRATIVE EMBODIMENT

A. General Description

With reference to the drawings in general, there is illustrated a system 10 and method in one form of the invention of utilizing eddy current impedance measuring techniques for detecting the induced change of the electrical conductivity and magnetic permeability due to residual stresses and defects in a manufactured part comprised of electrically conductive material. Broadly considered, an electro-magnetic transducer, such as an eddy current probe 12, is positioned near the surface of a part 14 for measuring induced eddy current signals. The probe 12 generates an electrical output signal representative of the sensed eddy current signals. Relative movement is effected between probe 12 and the part 14 by either moving probe 12 across the part or by moving part 14 with respect to probe 12. Such movement causes probe 12 to scan part 14 for producing electrical signals varying as a function of the sensed eddy currents, i.e., the eddy current signature. In response to the electrical signals from probe 12, an eddyscope 16 converts the electrical signals to mutually perpendicular drive signals representative of the eddy current impedance at a corresponding location. A first and second movement signal is generated by a numerical controller 18 for effecting movement of part 14 by energizing directional movement means 20 and 22. One of the first and second movement signal and eddyscope drive signals are combined in a signal mixer 24 for generating a composite signal which varies as a function of the movement of the probe and the measured eddy current signal. In response to the composite signal and the other of the movement signals, a display means 26 generates a pseudo three-dimensional image on the display means for mapping out stress distribution and defects of part 14.

Figure 2:
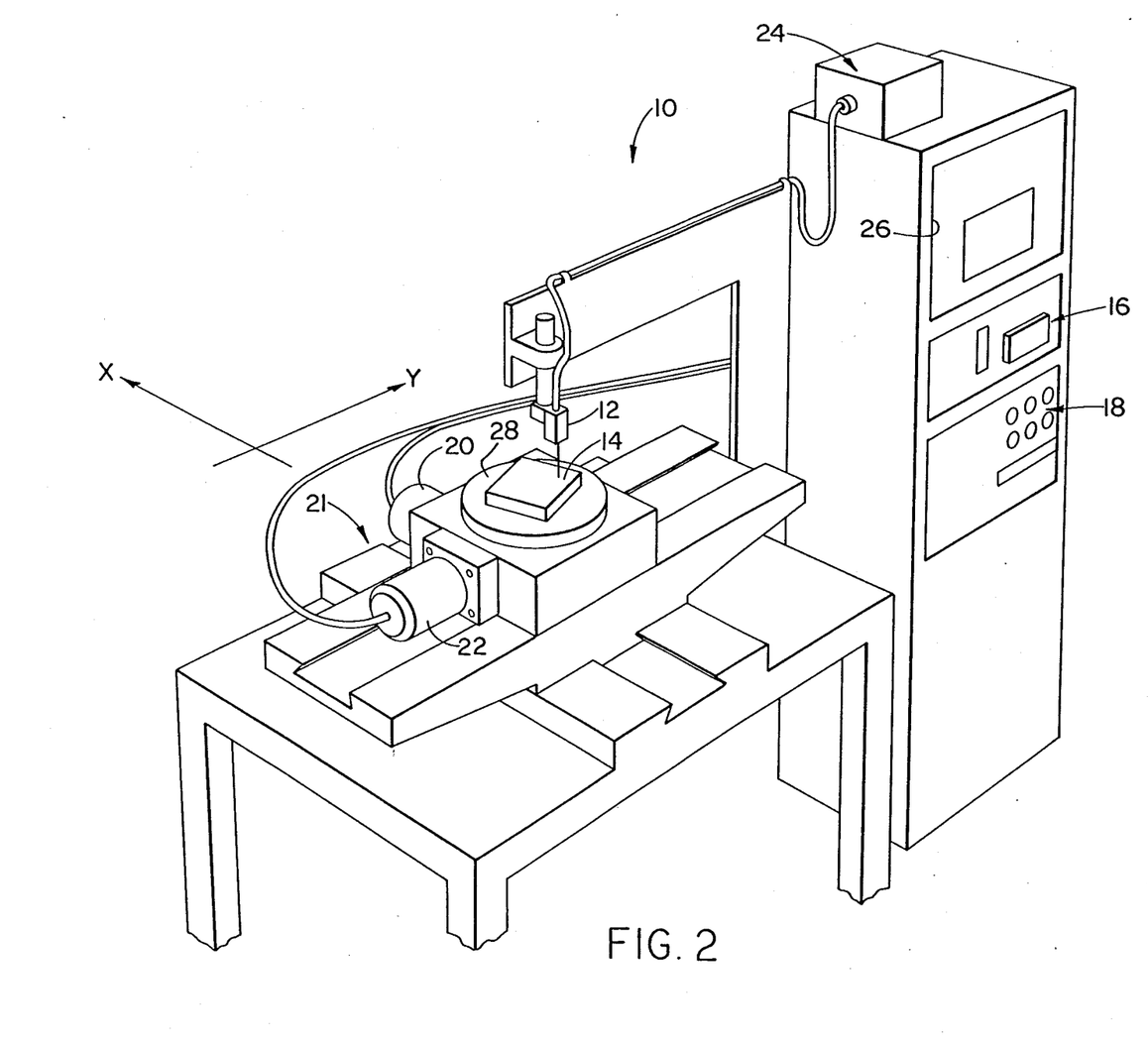
FIG. 2 shows the apparatus of the eddy current analysis system of the present invention.

More particularly and with specific reference to FIG. 2, a part 14 is scanned by eddy current probe 12 in an X-Y direction as illustrated. The system uses eddy current impedance measuring techniques for detecting induced changes of the electro-conductivity and magnetic permeability due to residual stresses and defects in the electrically conductive manufactured part.

Briefly, it is known that the measurement of flaws in a metal part by eddy currents involves the detection of variations of the currents induced in the part by the magnetic field of a primary winding traversed by an alternating exciting current. These induced currents produce a field which opposes the induction field which acts on the impedance of the secondary winding. The assembly of the primary and secondary windings forms the eddy current probe 12. Any defect or fault in the part occurring at the level of the sensor (change of dimension, variation in the electro-conductivity, variation in the magnetic permeability, cracks, etc.) modifies the phase of the intensity of the eddy currents and correlatively changes the impedance of the secondary winding.

For sensitivity reasons, the receiving coil is constituted by two secondary windings connected in opposition in such a way that the measuring signal is the asymmetrical voltage of the two windings. The measurement is differential if the two windings examine two adjacent areas of the part and is absolute if there is only one winding. The signal from the eddy current probe is amplified and converted into two mutually perpendicular drive signals containing phase and amplitude information by eddyscope 16. The drive signals typically are fed to the horizontal and vertical inputs of an oscilloscope. The two mutually perpendicular drive signals generated by the eddyscope 16 are fed to a signal mixer 24.

The depth penetration of the eddy current field in the material is inversely proportional to the square root of the conductivity, the permeability and the operating frequency. A calculation of the depth of penetration is made by means of the following formula:

$$t = 1/[(\pi f \mu \sigma)^{\frac{1}{2}}]$$

in which $\mu$=relative permeability, $\sigma$=conductivity, f=eddy current frequency and t=skin thickness of the conductor. The material surface of the desired depth thus can be examined by operating at a selective frequency. The frequencies used in the practice of this invention were two megahertz, one megahertz and 50 kilohertz. The eddy current probes used are standard absolute and differential probes, such as a SGE-9 eddy current probe manufactured by the Nortec Corporation. The eddyscope 16 used in the practice of this invention is a model NDT-25 programmable lab eddyscope manufactured by Staveley NDT Technologies, Inc.

For effecting relative motion between part 14 and probe 12, a programmable numerical controller 18 controls relative movement between the part and probe in two mutually perpendicular directions, illustrated as X and Y in FIG. 2. The numerical controller 18 as illustrated in FIG. 2 may take the form of a Unidex III Model programmable controller as manufactured by the Aerotech Corporation. The numerical controller includes a microcomputer which executes standard numerical control codes in a manner well known to those of ordinary skill in the art. These codes can be stored in the microcomputer memory for rapidly repeating an inspection. The numerical controller controls an X-Y scanner 21 including drive motors 20 and 22, and includes associated hardware and logic for interfacing the microcomputer for effecting drive control commands to motors 20 and 22. The X-Y scanner 21 positions part 14 for effecting measurements by probe 12. Positioning of part 14 is linear in the X and Y directions. In addition to controlling the position of the manufactured part 14, numerical controller 18 generates a first and second movement signal for representing respectively the Y direction and X direction movement of scanner 21. By securing manufactured part 14 at a known location on drive platform 28 the corresponding position of the part can be readily determined from the movement signals. The movement signals are applied to signal mixer 24 for generating composite signals.

Basically, numerical controller 18 controls an X-Y scanning motion of the manufactured part 14 relative to probe 12. The mechanical X and Y raster scanning voltage signals from the numerical controller 18 are inputs to the signal mixer 24. Additionally, the mutually perpendicular drive signals from eddyscope 16 are also applied to inputs of signal mixer 24. The signal mixer 24 combines the drive signals and the Y scanning voltage for producing a composite signal which is applied to a Y axis input of an X-Y plotter. The X scanning voltage signal is adjusted through signal mixer 24 and applied to a X axis input of an X-Y plotter. The resulting image generated by the plotter is a three-dimensional image in real time of the probe scanning across the surface of the manufactured part. The three-dimensional image obtained clearly shows residual stresses and surface defects. For a more detailed discussion of the three-dimensional images, reference is made to FIGS. 5–8.

B. Components of the System

Figure 3:
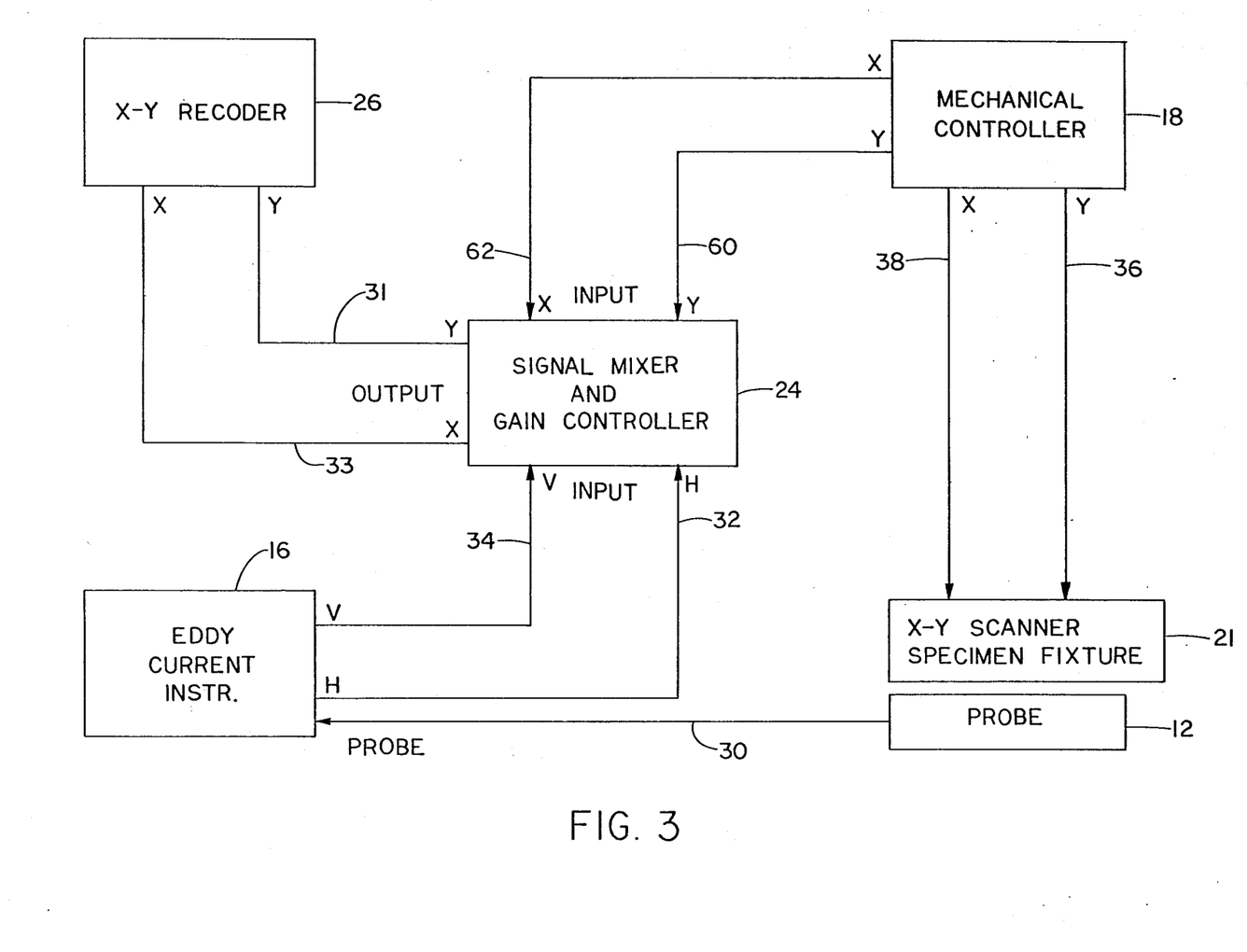
FIG. 3 is a block diagram of the eddy current analysis system.

Referring to FIG. 3, there is shown a block diagram of the eddy current system. The probe 12 outputs a signal on line 30 which is applied to an input of eddyscope 16. The eddyscope 16 generates a first drive signal on line 32 representing a horizontal deflection signal for an oscilloscope and a second drive signal on line 34 representing a vertical deflection signal for an oscilloscope. The first and second drive signals on lines 32 and 34 are applied to inputs of a signal mixer 24. A second set of inputs to signal mixer 24 are generated by the numerical controller 18 which represents the relative movement of the part versus the probe 12. In addition to generating relative motion signals applied to the inputs of the signal mixer 24, the numerical controller also provides motion commands on lines 36 and 38 to X-Y scanner 21. The X-Y scanner 21 as illustrated is a model ATS 406 manufactured by the Aerotech Corporation. The signal mixer 24 combines the signals applied to the inputs and generates a first and second composite signal on lines 31 and 33 respectively for driving an X-Y plotter 26. The X-Y plotter 26, as illustrated takes the form of a model 7045B X-Y plotter as manufactured by the Hewlett Packard Corporation.

C. Signal Mixer

Figure 4:
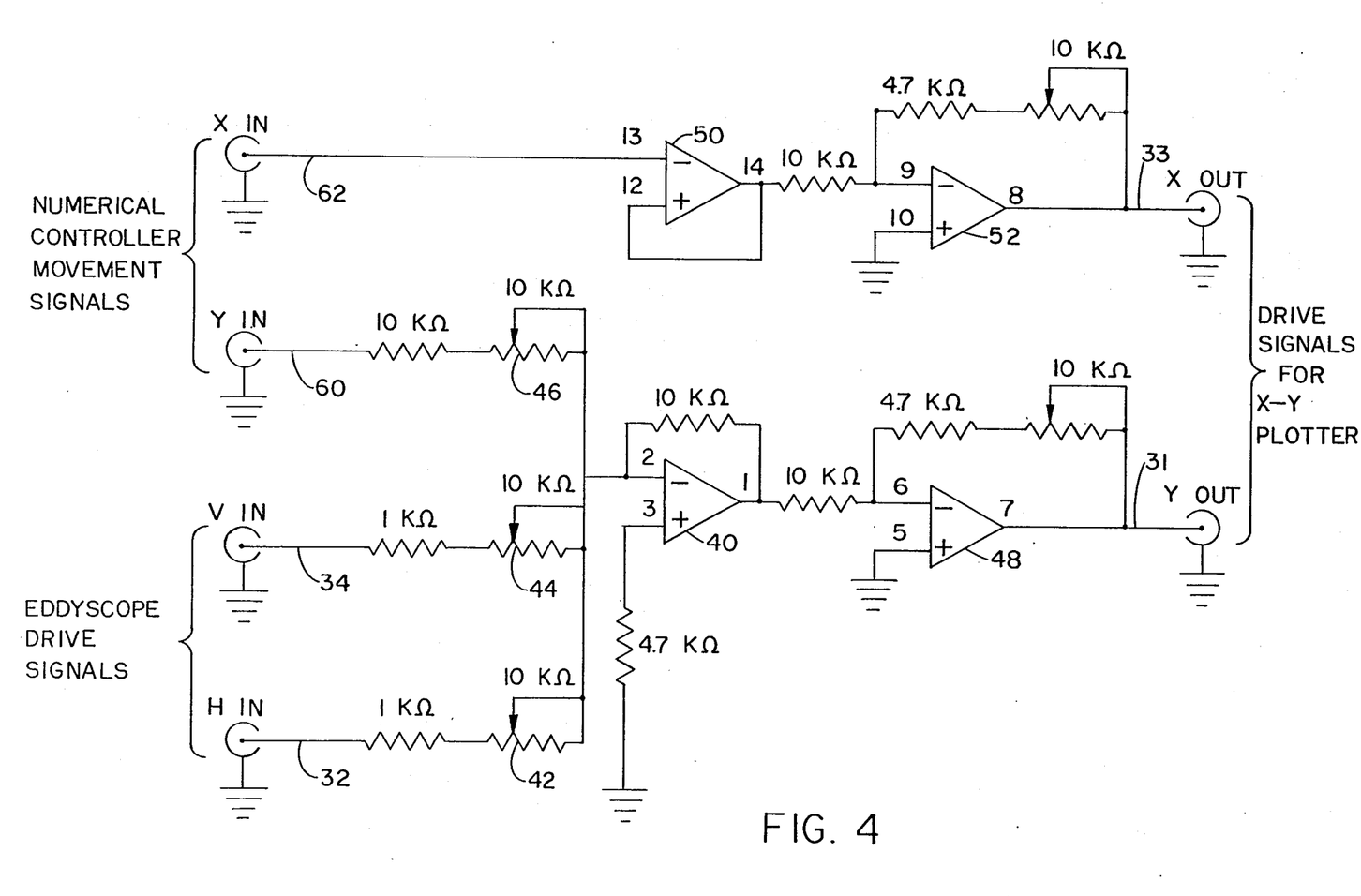
FIG. 4 is a schematic diagram of the signal mixer.
Figure 5A:
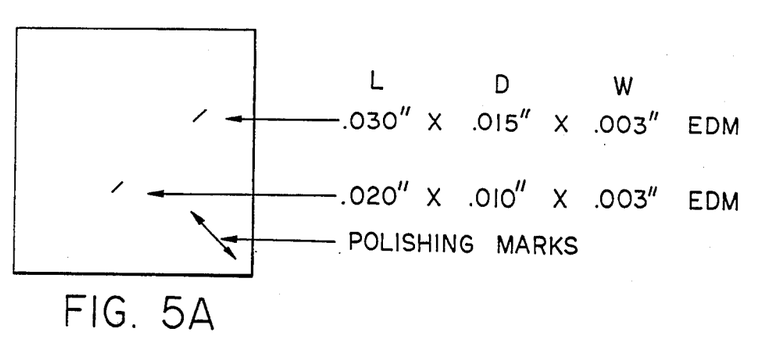
FIGS. 5A-B illustrate an image generated by the present invention for an electrostatic discharge machine notch in a part.
Figure 5B:
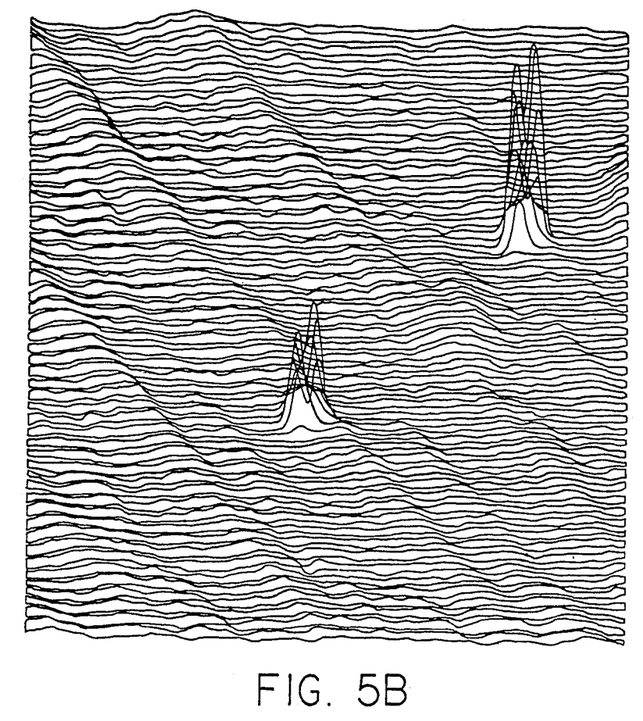

FIG. 4 shows a schematic diagram of signal mixer 24. Broadly considered, signal mixer 24 sums the drive signals from the eddyscope and the Y direction movement signal from the numerical controller and adjusts the value for applying to a Y axis input of the X-Y plotter. The X direction movement signal from the numerical controller is adjusted by signal mixer 24 for applying to X axis input of the X-Y plotter.

In particular, a three-input summing amplifier 40 amplifies and sums the inputs of the Y direction movement signal on line 60, the vertical drive signal on line 34 and the horizontal drive signal on line 32. The gain of each input can be individually adjusted respectively by adjustable resistors 46, 44, and 42. The output from amplifier 40 is applied to an input of amplifier 48 for adjusting the output of amplifier 40 to an appropriate level for Y axis input of the X-Y plotter.

The X direction movement signal on line 62 is applied to a unity gain inverting amplifier 50. Essentially, amplifier 50 is an inverter buffer. The output from amplifier 50 is applied to amplifier 52 for adjusting the gain of the output signal from amplifier 50. The output from amplifier 52 is applied to the X axis input of the X-Y plotter 26.

Thus, the output signal on line 31 applied to the Y axis of the plotter is the sum of the two mutually perpendicular drive signals and the relative Y direction movement of the scanner. The output signal applied to the X axis input of the plotter is an adjusted relative X-direction movement signal of the scanner 28. The resulting image generated on the plotter, maps out the residual stresses and surface defects in a pseudo-three-dimensional image as the part is scanned.

D. Operation of the System

In general, FIGS. 5–8 illustrate various defects displayed in a three-dimensional image according to the system and method of the present invention. In particular, FIGS. 5A–B show an image generated with the eddy current system of an electrostatic discharge machine notch. Since the eddy current inpedance measuring technique senses changes and variations of an induced electromagnetic field in metallic materials the depth of penetration can be varied as a function of the frequency for determining various defects. The hill-like display FIG. 5A clearly shows and identifies the EDM notch as shown in FIG. 5B.

Figure 6A:
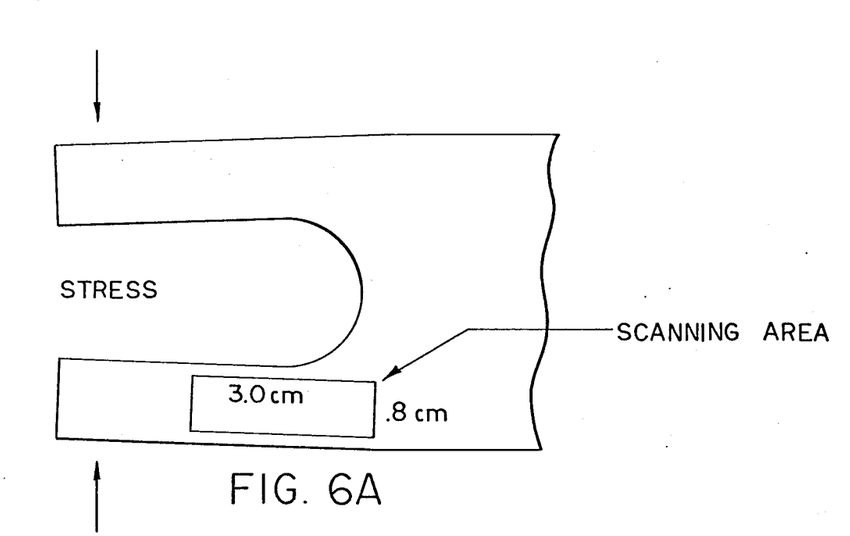
FIGS. 6A-B show the residual stresses in an image generated by the present invention by applying external stresses on the legs of an H-shaped aluminum part.
Figure 6B:
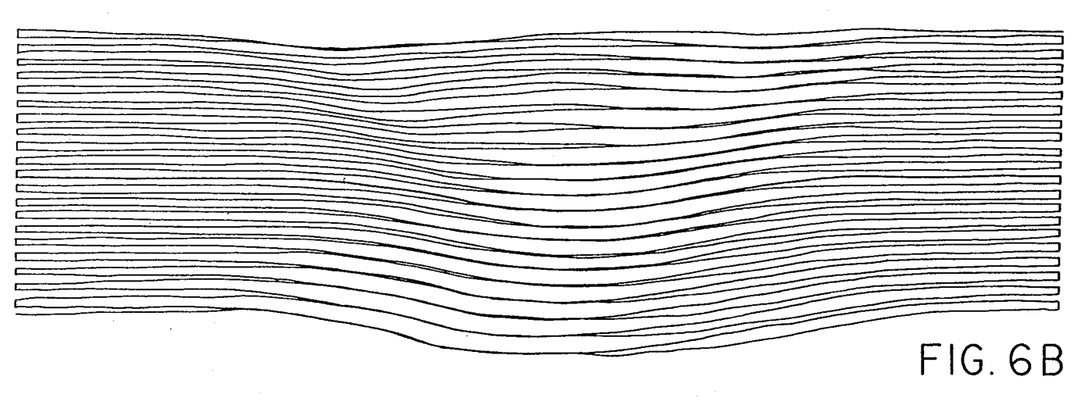
Figure 7A:
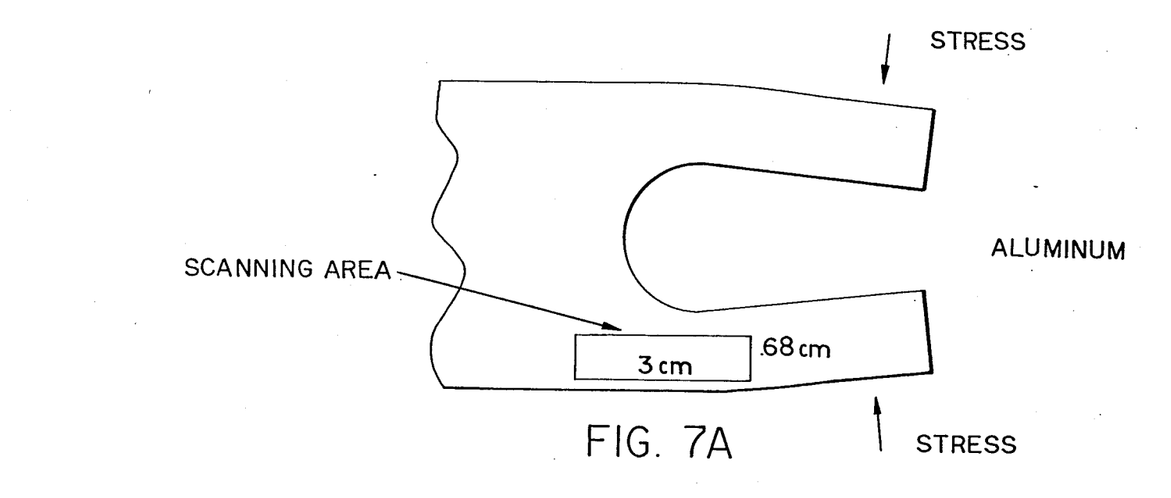
FIGS. 7A-B show the residual stresses in an image generated by the present invention by applying higher external stresses on the legs of the H-shaped aluminum part.
Figure 7B:
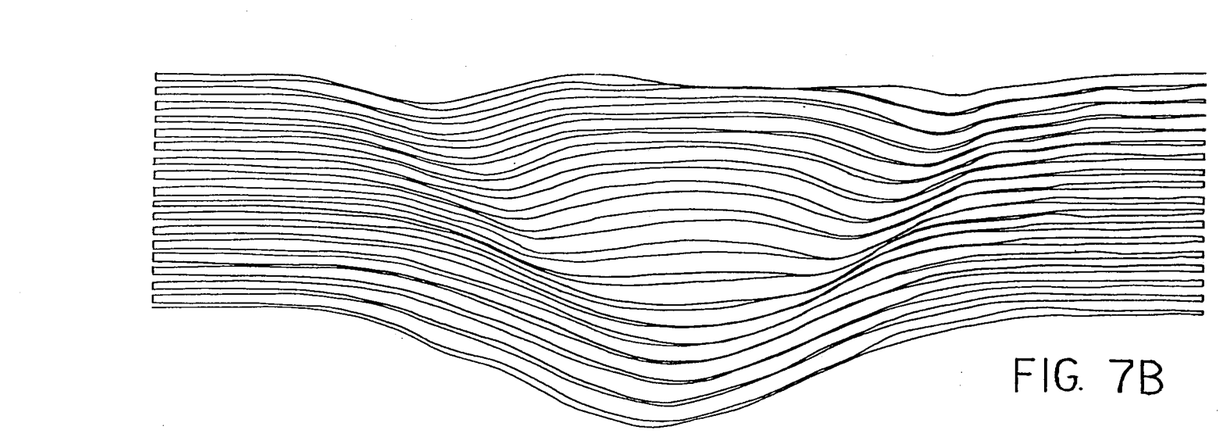
Figure 8A:
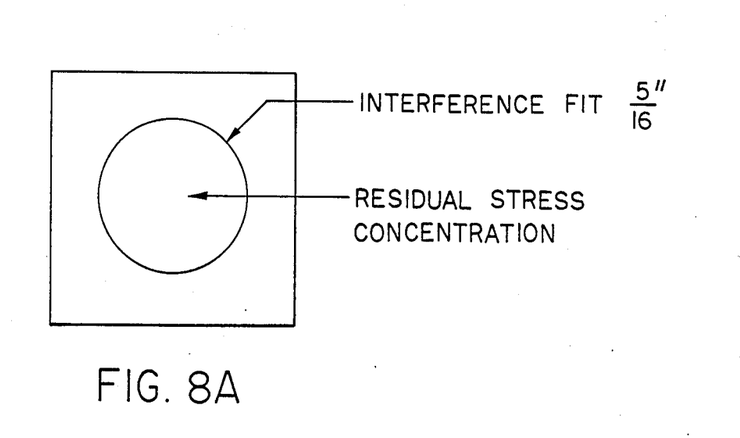
FIGS. 8A-B show the image for an interference fit for a plug in an aluminum plate.
Figure 8B:
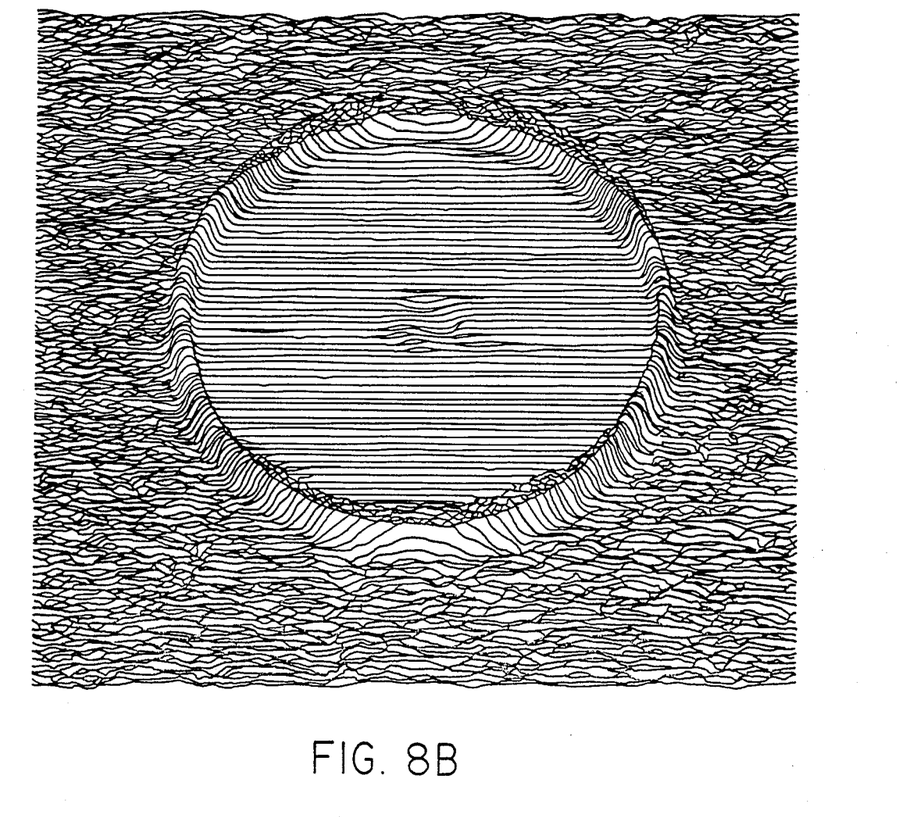

Localized static or dynamic stress concentrations generated by uneven distribution of applying residual stress cause fatigue cracks to initiate and propagate. The applied stresses and residual stresses induce electromagnetic changes in the material property. FIGS. 6 through 8 show the results of the eddy current inspection system for detecting changes in electro-magnetic properties of material under various stress variations. Using the mechanical scanning mechanism of the eddy current system, the stress distribution across the material surface is mapped out. The localized high stressed areas, i.e. potential crack initiation sites, can be readily identified from the mapped stress distribution as shown in FIGS. 6 through 8. In FIGS. 6A–B the residual stress distribution mapping of an area with residual stress is shown. The residual stress shown by the image in FIG. 6A is created by applying external stresses on the legs of an H-shaped aluminum part as shown in FIG. 6B.

FIGS. 7A–B show the residual stress distribution mapping of an area with higher external stresses applied. FIG. 7B shows that the residual stress is created by applying higher external stresses on the legs of an H-shaped aluminum specimen.

FIGS. 8A-B show the resulting three-dimensional image created by the eddy current system for an interference fit of a plug in an aluminum plate. The residual stress created on the edges and the center of the plug are clearly shown.

Figure 9A:
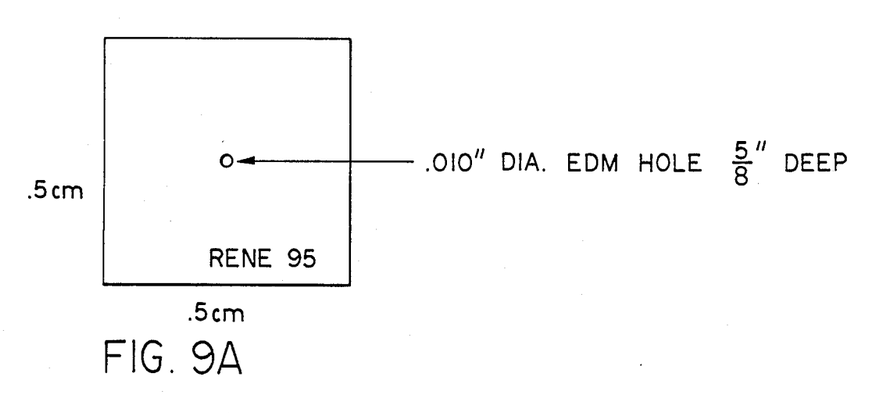
FIG. 9A-B show the eddy current system image for a 10 mil diameter hole on a 5 inch thick Rene 95 plate.
Figure 9B:
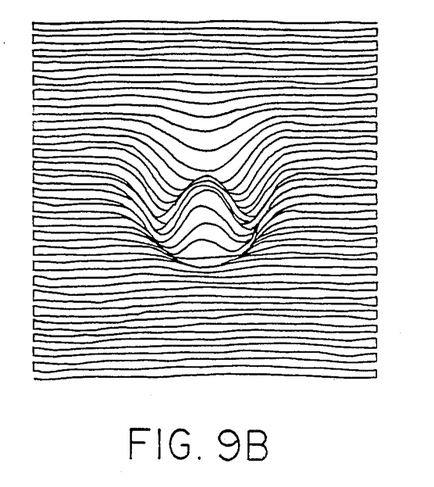
Figure 10:
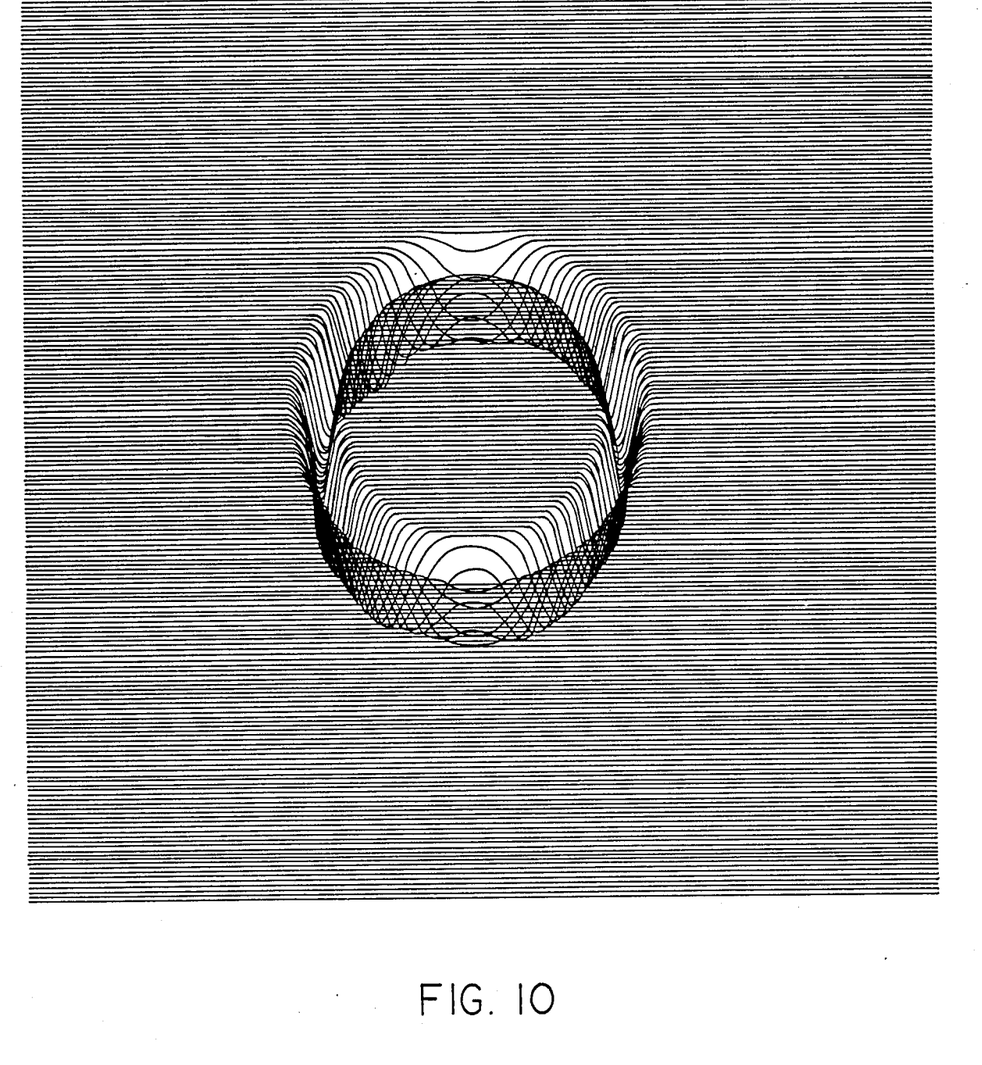
FIG. 10 shows an image for a closed round fatigue crack of infinite depth.

Surface breaks in defects such as porosities, fatigue cracks, and electrostatic discharge machine notches cause an abrupt change in the secondary electromagnetic field induced in the material by an eddy current sensor. The eddy current inspection system thus can detect the surface discontinuities by sensing the variations of eddy current responses. The previously mentioned surface discontinuities are all different in nature. For example, a fatigue crack which is a closed surface discontinuity has a higher frequency eddy current response than an open EDM notch. Signals from cracks, machine marks and geometric features can thus can be separated and catagorized. Referring to FIGS. 9A-B, there is shown the eddy current system image of a 10 mil diameter hole on a 5 inch thick Rene 95 plate. FIGS. 9A-B shows the signal response proportional to the size of the hole. FIG. 10 shows the electromagnetic image of another interference sample. This letter interference sample simulates a closed round fatigue crack of infinite depth.

As can be seen, the eddy current system not only locates the service defects, but displays the surface defects for easy identification and interpretation by a user of the system.

Also, in general, in one form of the invention, the invention makes use of the fact that irregularities are often known from previous experience to occur only in specific directions for a given part. The suspected areas of failure can be identified by destructively testing a plurality of parts for determining common mode fatigue failure and location. The eddy current probe is positioned in an area of the common mode of fatigue failure and location and the part is tested for defects. If any defects occur in the inspected area, the part can be quickly disposed of without the necessity of testing other areas for defects. Knowing the areas of suspected defects reduces inspection time in a system designed for inspecting a plurality of manufactured parts.

Upon identifying the suspected areas of failure, the microcomputer in the numerical controller can be programmed to scan this area. Numerous programs can be stored in the memory of the microcomputer representative of different suspected areas or different parts. Programming the microcomputer for inspecting a plurality of areas or parts decreased drastically the inspection time in a system for inspecting numerous parts.

E. Conclusion

There has been shown in general, in one form of the invention, an eddy current system for detecting changes in elecro-magnetic properties of the material. A scanning mechanism, coupled with the eddy current sensing probe easily maps out stress distribution across the material surface. Thus localized high stress areas of potential failure sites can be quickly identified.

The above described embodiment of the invention is illustrative only, and that modifications thereof may have occurred to those skilled in the art. Accordingly, this invention is not to be regarded as limited to the embodiment disclosed therein, but is to be limited as defined by the appended claims.

I claim:

1. An apparatus for non-destructive measuring and testing of a manufactured part comprising:
   an electromagnetic transducer positioned for inducing an eddy current in a part and for providing an output signal representative of the eddy current induced in the part;
   scanning apparatus connected to at least one of the part and said transducer for effecting relative movement between said transducer and the part;
   processing apparatus connected for receiving said output signal and for deriving therefrom first and second mutually perpendicular drive signals representative of phase and amplitude components of the eddy current;
   a controller coupled to said scanning apparatus for producing a first and a second movement signal for effecting relative movement between said transducer and the part;
   a signal mixer connected for receiving said drive signals and said movement signals and for generating a composite signal in response thereto, said composite signal being representative of the relative movement of said electromagnetic transducer in at least one axis as indicated by one of said movement signals and of the magnitude of said eddy current distributed in the part; and
   a two-dimensional display coupled for receiving and displaying said composite signal and the other movement signal to generate an apparent three-dimensional representative image of irregularities in the part.

2. The apparatus of claim 1 wherein said display includes:
   an X-Y plotter for plotting the three dimensional representative image in response to said composite signal.

3. The apparatus of claim 2 wherein said scanning apparatus includes a means for effecting movement of the part in mutually perpendicular directions.

4. The apparatus of claim 3 wherein said scanning means includes an X-Y scanner.

5. The apparatus of claim 1, wherein said electromagnetic transducer includes an absolute eddy current probe.

6. The apparatus of claim 1, wherein said electromagnetic transducer includes a differential eddy current probe.

7. The apparatus of claim 1, wherein said controller means includes a numerical controller for effecting operation of said scanning apparatus for moving the part into a selected position with respect to said transducer.

8. The apparatus of claim 7, wherein said numerical controller includes a microprocessor having a set of predetermined instructions for moving a predetermined area of the part adjacent said transducer.

9. The apparatus of claim 8, wherein said predetermined area is identified from destructively testing a plurality of parts for determining a common mode of fatigue failure and location thereof.

10. The apparatus of claim 9, wherein said microprocessor includes a memory means for storing said instructions.

11. The apparatus of claim 1, wherein said signal mixer includes means for summing said drive signals and first movement signal for producing said composite signal.

12. The apparatus of claim 11, wherein said signal mixer includes a three input summing amplifier having an adjustable gain.

13. The apparatus of claim 12, further including a means for amplifying said second movement signal, said amplification means having an adjustable gain.

14. The apparatus of claim 13, wherein said amplification means includes an analog amplifier.

15. A method for non-destructive testing of a part in a system including an eddy current probe for identifying irregularities in the part, said method comprising the steps of:

(a) positioning an eddy current probe near a surface of a part for detecting part irregularities manifested by variations in probe impedance, the probe generating electrical signals representative thereof;

(b) effecting relative movement between the probe and the part whereby the probe scans the part for producing electrical signals varying as a function of part irregularities;

(c) converting said electrical signals to two mutually perpendicular drive signals representative of the magnitude of the electrical signal at a corresponding location;

(d) generating a first and a second movement signal representative respectively of the probe position relative to the part along first and second orthogonal axes;

(e) generating a composite signal comprising a summation of the drive signals and the first movement signal; and (f) coupling the composite signal and the second movement signal to a display apparatus for generating a two-dimensional image representative of three-dimensional irregularities in the part.

16. The method of claim 15, further including the steps of:

(j) identifying a common mode of fatigue failure and location by destructively testing a plurality of parts;

(k) positioning the part to expose the part to the location determined in step (j) of identifying.

17. The method of claim 16, wherein the scanning apparatus includes a microcomputer having a memory, further including the step of storing instructions in the microcomputer for scanning the location determined in step (j) of identifying for testing a plurality of parts.

* * * * *